United States Patent [19]

Saito et al.

[11] Patent Number: 4,622,064
[45] Date of Patent: Nov. 11, 1986

[54] TRIAZOLO-(3,2-C)PERHYDROXAZIN-8-ONE DERIVATIVES AND USE AS FUNGICIDES AND PLANT GROWTH REGULATORS

[75] Inventors: Junichi Saito; Yoshio Kurahashi; Toshio Goto; Naoko Yamaguchi, all of Tokyo, Japan

[73] Assignee: Nihon Tokushu Noyaku Seizo K. K., Tokyo, Japan

[21] Appl. No.: 810,104

[22] Filed: Dec. 16, 1985

[30] Foreign Application Priority Data

Dec. 20, 1984 [JP] Japan .................. 59-267443

[51] Int. Cl.[4] ............... A01N 43/90; C07D 498/04
[52] U.S. Cl. ............................ 71/92; 514/236; 544/105; 71/76
[58] Field of Search ................. 544/105; 71/92, 76; 514/236

[56] References Cited

U.S. PATENT DOCUMENTS

| 3,952,002 | 4/1976 | Kramer et al. ............ 548/262 |
| 4,147,791 | 4/1979 | Meiser et al. ............ 514/383 |
| 4,203,995 | 5/1980 | Funaki et al. ............ 514/383 |
| 4,205,075 | 5/1980 | Baldwin et al. ........... 514/383 |
| 4,276,292 | 6/1981 | St. Georgiev et al. ..... 544/105 X |
| 4,486,218 | 12/1984 | Reiser et al. ............ 71/76 |

FOREIGN PATENT DOCUMENTS 2431407 1/1976 Fed. Rep. of Germany .

*Primary Examiner*—Richard L. Raymond
*Attorney, Agent, or Firm*—Sprung Horn Kramer & Woods

[57] ABSTRACT

Plant growth-regulating and fungicidally active triazolo-(3,2-c)perhydroxazin-8-ones of the formula

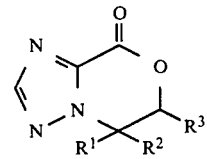

in which
$R^1$ represents a hydrogen atom,
$R^2$ represents a hydrogen atom a phenoxy group substituted by a halogen atom or a phenyl group, or a benyl group substituted by a halogen atom, or $R^1$, together with $R^2$, may form a halogen-substituted benzylidene group or a cyclohexyl-methylidene group, and
$R^3$ represents a tert-butyl group or a phenyl group substituted by a halogen atom.

10 Claims, No Drawings

TRIAZOLO-(3,2-C)PERHYDROXAZIN-8-ONE DERIVATIVES AND USE AS FUNGICIDES AND PLANT GROWTH REGULATORS

The present invention relates to novel triazolo-(3,2-c)perhydroxazin-8-one derivatives, to a process for their preparation, to their use as agricultural and horticultural fungicides and plant growth regulants.

It has already been disclosed that certain triazole derivatives have a function as agricultural and horticultural fungicides and/or plant growth regulants. (see Japanese Patent Laid-Open No. 111,477/1980)

There have been found novel triazolo-(3,2-c)perhydroxazin-8-one derivatives of the formula:

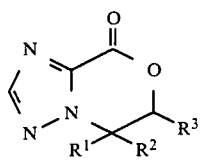

(I)

in which
$R_1$ represents a hydrogen atom,
$R_2$ represents a hydrogen atom, a phenoxy group substituted by a halogne atom or a phenyl group, or a benzyl group substituted by a halogen atom, or $R^1$, together with $R^2$, may form a halogen-substituted benzylidene group or a cyclohexyl-methylidene group, and
$R^3$ represents a tert-butyl group or a phenyl group substituted by a halogen atom.

Triazolo-(3,2-c)perhydroxazin-8-one derivatives of the formula (I) are obtained when the compounds of the formula (II):

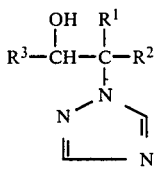

(II)

wherein $R^1$, $R^2$ and $R^3$ have the same meanings as above, are reacted with trichloromethyl chloroformate or phosgene, if appropriate in the presence of acid acceptors.

The novel triazolo-(3,2-c)perhydroxazin-8-one derivatives exhibit powerful fungicidal properties for agricultural and fungicidal use, as well as plant growth regulating properties.

Among the triazolo-(3,2-c)perhydroxazin-8-one derivatives according to the invention, of the formula (I), preferred compounds are those in which
$R_1$ represents a hydrogen atom,
$R_2$ represents a phenoxy group substituted by a halogen atom or a phenyl group, or a benzyl group substituted by a halogen atom, or
$R_1$ together with $R_2$ forms a halogen-substituted benzylidene group or cyclohexyl methylidene group, and
$R_3$ represents a tert-butyl group.

Very particularly preferred triazolo-(3,2-c)perhydroxazin-8-one derivatives of the formula (I) are those in which
$R_1$ represents a hydrogen atom,
$R_2$ represents a 4-chlorophenoxy group, a 4-biphenyl group or a 4-chlorobenzyl group, or $R_1$, together with $R_2$, forms a 4-chlorobenzylidene group or a cyclohexylmethylidene group; and
$R_3$ represents a tert-butyl group.

Specifically, the following compounds may be mentioned:

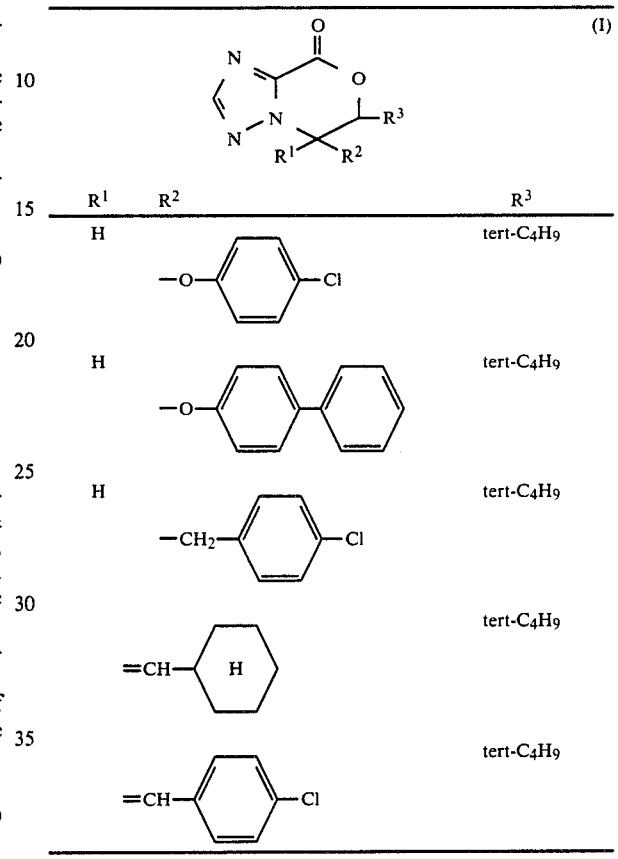

If, for example, 1-cyclohexyl-4,4-dimethyl-3-hydroxy-2(1H-1,2,4-triazol-1-yl)-pent-1-ene and trichloromethyl chloroformate are used as starting materials, the course of the process according to the invention can be represented by the following equation:

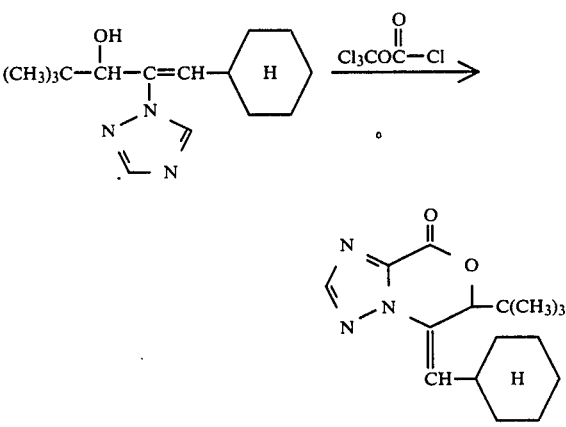

In the formula (II), $R^1$, $R^2$ and $R^3$ preferably have the meaning already each given above.

The compounds of formula (II) usable according to the invention are already known. (see Japanese Patent Laid-Open No. 111477/1980, Japanese Patent Laid-Open No. 41875/1979, Japanese Patent Laid-Open No. 28170/1978, Japanese Patent Laid-Open No. 80738/1973, Japanese Patent Laid-Open No. 13534/1975 and Japanese Patent Laid Open No. 23267/1976)

As examples there may be mentioned:
1-cyclohexyl-4,4-dimethyl-3-hydroxy-2-(1H-1,2,4-triazol-1-yl)pent-1-ene, 1-(4-chlorophenoxy-3,3-dimethyl-1-(1H-1,2,4-triazol-1-yl)-butan-2-ol, 1-(4-phenyl-phenoxy)-3,3-dimethyl-1-(1H-1,2,4-triazol-1-yl)-butan-2-ol, 1-(4-chlorophenyl)-4,4-dimethyl-2-(1H-1,2,4-triazol-1-yl)-pentan-3-ol, and 1-(4-chlorophenyl)-4,4-dimethyl-3-hydroxy-2-(1H-1,2,4-triazol-1-yl)-pent-1-ene.

Phosgene may also be used in the same manner instead of trichloromethyl chloroformate as the starting material.

Suitable diluents are all inert organic solvents as well as water. Preferred diluents include water; aliphatic, cycloaliphatic and aromatic hydrocarbons (which may optionally be chlorinated), for example, hexane, cyclohexane, petroleum ether, ligroin, benzene, toluene, xylene, methylene chloride, chloroform, carbon tetrachloride, ethylenechloride, trichloroethylene and chlorobenzene; ether, for example, diethyl ether, methyl ethyl ether, di-iso-propyl ether, dibutyl ether, propylene oxide, dioxane and tetrahydrofuran; ketone, for example, acetone, methyl ethyl ketone, methyl-iso-propyl ketone and methyl-iso-butyl ketone; nitriles, for examples, acetonitrile propionitrile and acrylonitrile; alcohols, for example, methanol, ethanol, iso-propanol, butanol and ethylene glycol; esters, for example, ethyl acetate and amyl acetate; acid amides, for example, dimethyl formamide and dimethyl acetamide; sulfones and sulfoxides, for example, dimethyl sulfoxide and sulfolan and bases, for example, pyridine.

Further, the reaction according to the present invention can be carried out in the presence of an acid acceptor. Such acid acceptor can include hydroxides, carbonates, bicarbonates and alcoholates of alkali metals, tertiary amines, for example, triethylamine, diethylaniline and pyridine.

The reaction temperature can be varied within a substantial range. In general, the reaction is carried out at between $-20°$ C. and the boiling point of the mixture and preferably between $0°$ C. and the boiling point of the reaction mixture.

The reaction can be carried out under an ambient pressure or under elevated pressure or reduced pressure.

In carrying out the process for preparation of the compounds according to the invention, there are employed, per mole of the compound of formula (II), about 0.5–1.5 mole, preferably about 1–1.2 mole of trichloromethyl chloroformate in an inert solvent (diluent) and if appropriate in the presence of about 2 mole of an acid acceptor (e.g. pyridine) and at a temperature of about $0°$–about $5°$ C.

Moreover, the reaction temperature in the reaction step of trichloromethyl chloroformate is preferably between about $0°$–about $5°$ C. and it may be raised to a refluxing temperature after the completion of the reaction.

The active substances according to the invention can be employed in plant protection for combating Plasmodiophoromycetes, Oomycetes, Chytridiomycetes, Zygomycetes, Ascomycetes, Basidiomycetes and Deuteromycetes, for instance, cucumber powder mildew (*Sphaerotheca fuliginea*), barley powder mildew (*Erysiphe graminis*) and leaf rust (*Puccinia recondita*).

The active compounds according to the invention engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

Plant growth-regulating compounds can be employed, for example, to inhibit the vegetative growth of the plants. such inhibition of growth is inter alia of economic interest in the case of grasses, since it is thereby possible to reduce the frequency of cutting the grass in ornamental gardens, parks and sportsgrounds, at verges, at airports or in fruit orchards. The inhibition of growth of herbaceous and woody plants at verges and in the vicinity of pipelines or overland lines or, quite generally, in areas in which heavy additional growth of plants in undesired, is also of importance.

The use of growth regulators to inhibit the growth in length of cereals is also important. The danger of lodging of the plants before harvesting is thereby reduced or completely eliminated. Furthermore, growth regulators can strengthen the stem of cereals, which again counteracts lodging. Use of growth regulators for shortening and strengthening the stem enables higher amounts of fertilizer to be applied to increase the yield, without danger of the cereal lodging.

In the case of many crop plants, inhibition of the vegetative growth makes denser planting possible, so that greater yields per area of ground can be achieved. An advantage of the smaller plants thus produced is also that the crop can be worked and harvested more easily.

Inhibition of the vegetative growth of plants can also lead to increases in yield, since the nutrients and assimilates benefit blossoming and fruit formation to a greater extent than they benefit the vegetative parts of plants.

Promotion of vegetative growth can also frequently be achieved with growth regulators. This is of great utility if it is the vegetative parts of the plants which are harvested. Promoting the vegetative growth can, however, also simultaneously lead to a promotion of generative growth, since more assimilates are formed, so that more fruit, or larger fruit, is obtained.

Increases in yield can in some cases be achieved by affecting the plant metabolism, without noticeable changes in vegetative growth. A change in the composition of plants, which in turn can lead to a better quality of the harvested products, can furthermore be achieved with growth regulators. Thus it is possible, for example, to increase the content of sugar in sugar beet, sugar cane, pineapples and citrus fruit or to increase the protein content in soya or cereals. Using growth regulators it is also possible, for example, to inhibit the degradation of desired constituents, such as, for example, sugar in sugar beet or sugar cane, before or after harvesting. It is also possible favourably to influence the production or the efflux of secondary plant constituents. The stimulation of latex flux in rubber trees may be mentioned as an example.

Parthenocarpous fruit can be formed under the influence of growth regulators. Furthermore, the gender of the flowers can be influenced. Sterility of the pollen can also be produced, which is of great importance in the breeding and preparation of hybrid seed.

Branching of plants can be controlled by using growth regulators. On the one hand, by breaking the apical dominance the development of side shoots can be promoted, which can be very desirable, especially in the cultivation of ornamental plants, also in connection with growth inhibition. On the other hand, however, it is also possible to inhibit the growth of side shoots. There is great interest in this action, for example, in the cultivation of tobacco or in the planting of tomatoes.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The shedding of fruit can also be controlled with growth regulators. On the one hand, it is possible to prevent premature shedding of fruit. However, on the other hand, shedding of fruit, or even the fall of blossom, can be promoted up to a certain degree (thinning out) in order to interrupt the alternance. By alternance there is understood the peculiarity of some varieties of fruit to produce very different yields from year to year, for endogenic reasons. Finally, using growth regulators, it is possible to reduce the force required to detach the fruit at harvest time so as to permit mechanical harvesting or facilitate manual harvesting.

Using growth regulators, it is furthermore possible to achieve an acceleration or retardation of ripening of the harvest product, before or after harvesting. This is of particular advantage, since it is thereby possible to achieve optimum adaptation to market requirements. Furthermore, growth regulators can at times improve the coloration of fruit. In addtion, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators, it is furthermore possible to influence the latent period of seeds or buds of plants, so that the plants, such as, for example, pineapple or ornamental plants in nurseries, germinate, shoot or blossom at a time at which they normally show no readiness to do so. Retarding the shooting of buds or the germination of seeds with the aid of growth regulators can be desirable in regions where frost is a hazard, in order to avoid damage by late frosts.

Finally, the resistance of plants to frost, drought or a high salt content in the soil can be induced with growth regulators. Cultivation of plants in regions which are usually unsuitable for this purpose thereby becomes possible.

The good toleration by plants of the active compounds at the concentrations required for combating plant diseases, permits treatment of above-ground parts of plants of vegetative propagation stock and seeds, and of the soil.

The active compounds can be converted into the customary formulations, such as solutions, emulsions, suspensions, powders, foams, pastes, granules, aerosols, natural and synthetic materials impregnated with active compound,. very fine capsules in polymeric substances, coating compositions for use on seed, and formulations' used with burning equipment, such as fumigating cartridges, sumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, there are suitable in the main, aromatic hydrocarbons, such as xylene, toluene or alkyl naphthalenes, chorinated aromatic or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulation.

It is possible to use colorants such as inorganic pigments, for example iron oxide, titanium oxide and prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations or in the various use forms as a mixture with other known active compounds, such as fungicides, bactericides, insecticides, acaricides, nematicides, herbicides, bird repellents, growth regulants, plant nutrients and agents for improving soil structure.

The active compounds can be used as such or in the form of their formulations or the use forms prepared there-from by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the case of using the compounds according to the invention as agricultural and horticultural fungicides, in the treatment of parts of plants, the active compound concentrations in the use forms can be varied within a substantial range. They are, in general, from 1 to 0.0001% by weight, preferably from 0.5 and 0.001%.

For the treatment of seed, amounts of active compound of 0.001 to 50 g, especially 0.01 to 10 g, are generally employed per kilogram of seed.

For the treatment of soil, active compound concentrations, at the point of action, of 0.00001 to 0.1% by weight, especially of 0.0001 to 0.02%, are generally employed.

In the case of using the compounds according to the invention as plant growth regulants, the amounts applied can be varied within a substantial range. In general, about 0.005 to about 10 kg, preferably 0.01 to 5 kg, of the active compound are employed per hectare of soil surface.

As regards the time of application, the rule is that the growth regulators are applied within a preferred period of time, the exact definition of which depends on the climatic and vegetative circumstances.

The following examples illustrate the present invention specifically. It should be understood however that the present invention is in no way limited to them alone.

PREPARATION EXAMPLE

Example 1

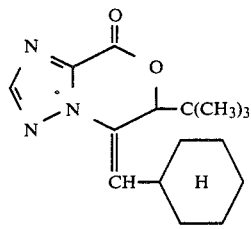

(Compound No. 1)

2.63 g of 1-cyclohexyl-4,4-dimethyl-3-hydroxy-2-(1H-1,2,4-triazol-1-yl)-pent-1-ene and 1.58 g of pyridine were dissolved in 30 ml of dichloromethane, to which were added dropwise 1.98 g of trichloromethyl chloroformate dissolved in 5 ml of dichloromethane under ice cooling. Then, after stirring at room temperature for one hour, the dichloromethane layer was washed with water, dried and then dichloromethane was distilled off under a reduced pressure to obtain 2.25 g of the crude desired product. Further, by purifying by column chromatography (hexane: ethyl acetate=2:1), 1.92 g of the desired 5-cyclohexyl methyl idene-6-tert.-butyl-(1,2,4)-triazolo-(3,2-c)-perhydroxazin-8-one were obtained. $n_D^{28}$ 1.5264.

The compounds according to the present invention which were synthesized in the same manner as in Example 1 are shown in Table 1.

TABLE 1

| Compound No. | $R^1$ | $R^2$ | $R^3$ | Physical constant |
|---|---|---|---|---|
| 2 | H | H | tert-$C_4H_9$ | mp. 143–150° C. |
| 3 | H | H | ![Cl-phenyl-Cl] | mp. 172–185° C. |
| 4 | H | $-O-\text{phenyl}-Cl$ | tert-$C_4H_9$ | mp. 210–211° C. |
| 5 | H | $-O-\text{phenyl-phenyl}$ | tert-$C_4H_9$ | oil |
| 6 | H | $-CH_2-\text{phenyl}-Cl$ | tert-$C_4H_9$ | mp. 141–143° C. |
| 7 | $=CH-\text{phenyl}-Cl$ | | tert-$C_4H_9$ | mp. 140–141° C. |

USE EXAMPLE

Example 2

Controlling test for powdery mildew on cucumber

Test Method

A test compound in the form of emulsion was sprayed by using a spray gun to cucumber plant (variety: Tokiwajibai) at 2-leaf stage cultured in a porous pot 9 cm in diameter. One day after the spraying, the suspension of spore of the pathogen (Sphaerotheca fuliginea) was inoculated by spraying. After leaving in a thermostable chamber at 23° C., the degree of infection-was determined based on the rate of lesion area at 10th day to calculate the controlling effect.

| Infection degree | Rate of lesion area (%) |
|---|---|
| 0 | 0 |
| 0.5 | less than 2 |
| 1 | 3–5 |
| 2 | 6–15 |
| 3 | 16–30 |
| 4 | 31–50 |
| 5 | more than 51 |

$$\text{Control Value (\%)} = \frac{\begin{pmatrix}\text{infection} \\ \text{degree in} \\ \text{not-treated Plot}\end{pmatrix} - \begin{pmatrix}\text{infection} \\ \text{degree in} \\ \text{treated Plot}\end{pmatrix}}{\text{infection degree in not-treated Plot}} \times 100$$

The active compounds according to the present invention exhibited 100% controlling effect at the concentration of the effective ingredient of less than 50 ppm.

Example 3

Growth controlling test for rice plant

Preparation of active compound (emulsion)

Active compound: 1 part by weight
Carrier, acetone: 5 part by weight
Emulsifier, benzyloxypolyglycol ether: 1 part by weight A predetermined amount of the thus formulated chemical was diluted with water and served for the test.

Test Method

Soils of paddy field were filled in a pot of 20 cm×25 cm×9 cm, into which were transplanted seedlings of paddy rice at 2-3 leaf stage (variety: Koshihikari), and then water was flooded to about 3 cm depth. Five days after the transplantation a predetermined amount of the active compound was added dropwise for treatment to the water surface by using a pipette. Then, the flooded state was kept at about 3 cm depth and, 20 days after the chemical treatment, the height of the rice plants was measured and compared with that of the rice plants in the not-treated lot to calculate the growth controlling rate. The results are shown in Table 2.

TABLE 2

| Compound No. | Effective ingredient amount kg/ha | Inhibition of growth in % |
|---|---|---|
| 1 | 2.0 | 66.3 |
|   | 0.5 | 35.2 |
|   | 0.25 | 23.1 |
| 6 | 2.0 | 73.2 |
|   | 0.5 | 51.6 |
|   | 0.25 | 37.8 |
| 7 | 2.0 | 78.4 |
|   | 0.5 | 49.8 |
|   | 0.25 | 46.4 |

It will be appreciated that the instant specification and examples are set forth by way of illustration and not limitation, and that various modifications and changes may be made without departing from the spirit and scope of the present invention.

We claim:

1. A triazolo-(3,2-c)perhydroxazin-8-one derivative of the formula:

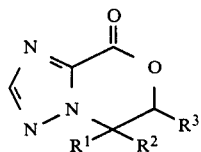

in which
$R^1$ represents a hydrogen atom,
$R^2$ represents a hydrogen atom, a phenoxy group substituted by a halogen atom or a phenyl group, or a benzyl group substituted by a halogen atom, or $R^1$, together with $R^2$, may form a halogen-substituted benzylidene group or a cyclohexyl-methylidene group, and
$R^3$ represents a tert-butyl group or a phenyl group substituted by a halogen atom.

2. A compound according to claim 1, in which
$R^1$ represents a hydrogen atom,
$R^2$ represents a phenoxy group substituted by a halogen atom or a phenyl group, or a benzyl group substituted by a halogen atom, or $R^1$, together with $R^2$, forms a halogen-substituted benzylidene group or a cyclohexylmethylidene group, and
$R^3$ represents a tert-butyl group.

3. A compound according to claim 1, in which
$R^1$ represents a hydrogen atom,
$R^2$ represents a 4-chlorophenoxy group, a 4-biphenyl group or a 4-chlorobenzyl group, or $R^1$, together with $R^2$, form a 4-chlorobenzylidene group or a cyclohexylmethylidene group, and
$R^3$ represents a tert-butyl group.

4. A compound according to claim 1, wherein such compound is 5-(4-chlorophenoxy)-6-tert-butyl-(1,2,4)-triazolo-(3,2-c)perhydroxazin-8-one of the formula:

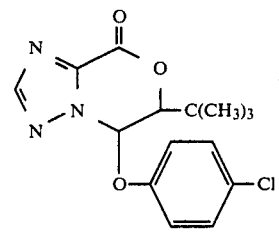

5. A compound according to claim 1, wherein such compound is 5-cyclohexyl-methylidene-6-tert.-butyl-(1,2,4)-triazolo-(3,2-c)perhydroxazine-8-one of the formula:

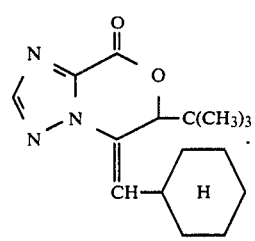

6. A plant growth-regulating or fungicidal composition comprising a plant growth-regulating or fungicidally effective amount of a triazolo-(3,2-c)perhydroxazin-8-one according to claim 1 and a diluent.

7. A method of regulating the growth of plants which comprises applying to such plants or to a plot in which said plants are grown or to be grown a plant growth-regulating effective amount of a compound according to claim 1.

8. The method according to claim 7, wherein such compound is
5-(4-chlorophenoxy)-6-tert-butyl-(1,2,4)-triazolo-(3,2-c)perhydroxazin-8-one, or
5-cyclohexyl-methylidene-6-tert-butyl-(1,2,4)-triazolo-(3,2-c)perhydroxazine-8-one.

9. A method of combating fungi which comprises applying to such fungi or to a fungus habitat a fungicidally effective amount of a compound according to claim 1.

10. The method according to claim 9, wherein such compound is
5-(4-chlorophenoxy)-6-tert-butyl-(1,2,4)-triazolo-(3,2-c)perhydroxazin-8-one, or
5-cyclohexyl-methylidene-6-tert-butyl-(1,2,4)-triazolo-(3,2-c)perhydroxazine-8-one.

* * * * *